United States Patent [19]
Yagi et al.

[11] Patent Number: 4,810,295
[45] Date of Patent: Mar. 7, 1989

[54] IMPRESSION COMPOSITION

[75] Inventors: Toshiharu Yagi, Takarazuka; Yoshihide Higashihata, Settsu; Hiromichi Sakuma, Settsu; Yoshito Tanaka, Settsu; Jouji Saito, Settsu; Minako Inomata, Osaka; Torahiko Nagano, Takatsuki; Takashi Nishioka, Sakai; Sumiko Yubara, Osaka, all of Japan

[73] Assignee: Daikin Industries, Ltd., Osaka, Japan

[21] Appl. No.: 111,646

[22] Filed: Oct. 23, 1987

[30] Foreign Application Priority Data

Oct. 24, 1986 [JP] Japan ................................ 61-254470

[51] Int. Cl.$^4$ ............................ C08L 1/00; C08L 1/26
[52] U.S. Cl. ................................. 106/38.51; 106/209; 106/197.2
[58] Field of Search .................. 106/38.51, 209, 197.2

[56] References Cited

U.S. PATENT DOCUMENTS 2,568,752  9/1951  Lochridge ........................... 106/209
2,657,971  11/1953  Lochridge ......................... 106/197.2

Primary Examiner—Theodore Morris
Attorney, Agent, or Firm—Armstrong, Nikaido Marmelstein & Kubovcik

[57] ABSTRACT

The present invention provides an impression composition of the alginate type which comprises (a) an alginate, (b) calcium sulfate and/or lead silicate, and (c) a filler as its main components and which is characterized in that the alginate component comprises in combination an alginate having a distribution of molecular weights in a lower range and an alginate having a distribution of molecular weights in a higher range.

4 Claims, No Drawings

IMPRESSION COMPOSITION

The present invention relates to an impression composition of the alginate type.

Dental impression materials are used for preparing, for example, an impression of a decayed tooth to remedy the tooth. Impression materials include those of the alginate type, silicon type and polysulfide type. In view of economy and ease of handling, alginate impression materials are generally used.

Many characteristics are required of impression materials. For example, they must have a dust-free property, be compatible with water and easy to knead, possess high rubber elasticity and high strength, exhibit a smooth texture on gelation, afford smooth-surfaced plaster models and be readily usable in combination with ager. However, none of the conventional impression materials fulfill all of these requirements.

The main object of the present invention is to provide an impression composition which fulfills all the characteristics required of impression materials, such as dust-free property, ease of kneading, rubber elasticity, strength, surface smoothness or gloss and amenability to combination use.

The above and other objects of the invention will become apparent from the following description.

The present invention provides an impression composition of the alginate type which comprises (a) an alginate, (b) calcium sulfate and/or lead silicate, and (c) a filler as its main components and which is characterized in that the alginate component comprises in combination an alginate having a distribution of molecular weights in the lower range and an alginate having a distribution of molecular weights in the higher range.

Examples of alginates (a), calcium sulfates (b) and fillers (c) useful for the invention are those already known for use in conventional alginate impression materials. More specifically, suitable examples are sodium alginate, potassium alginate and alginic acid triethanolamine and like alginates, and calcium sulfate dihydrate, calcium sulfate hemihydrate, anhydrous calcium sulfate and like calcium sulfates. Lead silicate is usable singly or in combination with such a calcium sulfate. Examples of suitable fillers are kieselguhr, talc, silica, aluminum hydroxide and the like.

The amount of components to be used in the invention are not limited specifically but can be determined from the ranges already known. It is especially suitable to use, for example, 5 to 25 wt. % of the component (a), 5 to 30 wt. % of the component (b) and the balance the filler, based on the combined amount of the three components.

The impression composition of the present invention is characterized in that the component (a) comprises in combination an alginate having a distribution of molecular weights in the lower range (hereinafter referred to as "low-molecular-weight alginate") and an alginate having a distribution of molecular weights in the higher range (hereinafter referred to as "high-molecular-weight alginate"). The low-molecular-weight alginate is selected from among those having a viscosity of about 50 to about 900 cps as measured at 25° C. using a B-type rotation viscometer when in the form of a 1% aqueous solution. The high-molecular-weight alginate is selected from among those having a viscosity of about 150 to about 1000 cps as measured under the same conditions as above. Such two alginates which differ from each other by at least about 100 cps, preferably at least about 200 cps, in viscosity are used in combination.

In the invention, the proportion of the low-molecular-weight alginate and the high-molecular-weight alginate is preferably in the range of 10:90 to 90:10 in weight ratio.

We have further conducted research on useful alginates and found that when the alginic acid molecules present in the composition are up to 1 in the ratio of D-mannuronic acid (hereinafter abbreviated as "M") to L-gluronic acid (hereinafter abbreviated as "G"), i.e. in M/G ratio, the composition exhibits improved properties in respect of strain in compression, permanent deformation, compressive strength, etc. The M/G ratio was measured according to the method described in Acta Chemica Scandinavica 16, (1962) No. 8, p 1908–1918. With the present invention, the M/G ratio is more preferably in the range of 0.3 to 1, most preferably in the range of 0.5 to 1.

According to the present invention, materials other than the foregoing components, such as magnesium oxide and zinc oxide, can be added to the impression composition in an amount of 0.1 to 20 wt. % to reduce the permanent deformation of the composition as kneaded. It is also possible to incorporate hexafluorotitanates, hexafluorozirconates and the like into the impression composition in order to assure the kneaded composition of reduced permanent deformation while minimizing the reduction in the strain thereof in compression and to give improved surface smoothness and gloss to plaster model prepared from the impression. To a suitably adjust the gelation time, for example, to about 1 to about 5 minutes and thereby render the composition easy to handle, it is also desirable to add to the composition phosphates such as tertiary phosphates, pyrophosphates, tripolyphosphates and hexametaphosphate, oxalates, carbonates, etc. Such phosphates, oxalates and carbonates are used preferably in an amount of 0.05 to 5.0 wt. % based on the composition.

The components of the present composition can be mixed together by a known method of mixing powders or mixing powder and liquid. For example, the components are mixed together in a mixer or mixed together while being pulverized in a crusher-mixer.

The impression composition of the invention is usable for preparing various impressions. For example, for dental treatments and remedies, the composition is usable for preparing impressions of teeth. Further in making molds for metal casting, the composition is usable for preparing patterns of the configuration to be cast. In molding plastics, the impression is usable for preparing patterns of the shape to be molded.

The impression composition of the present invention fulfills all the characteristics required of impression materials, such as dust-free property, ease of kneading, rubber elasticity, strength, surface smoothness and gloss, and amenability to combination use. Thus, the present composition is compatible with water to give a uniform paste rapidly, kneadable free from dust, affords smooth-surfaced plaster models and is readily usable in combination with agar. The composition has high rubber elasticity and strength and therefore assures very high dimensional stability. For example, the composition has outstanding characteristics of at least 10% in strain in compression, up to 3% in permanent deformation and at least 5000 g in compressive strength as measured according to JIS T 6505.

The invention will be described with reference to the following examples and comparative examples, in which percentages, other than those listed in Table 1, are all by weight.

EXAMPLE 1

An impression composition was prepared from 10% of sodium alginate (M/G ratio 1.3) having a viscosity of 100 cps (viscosity of 1% aqueous solution thereof as measured at 25° C. by a B-type rotation viscometer, the same as hereinafter), 3% of sodium alginate (M/G ratio 1.3) having a viscosity of 600 cps, 12% of anhydrous calcium sulfate, 1% of anhydrous $Na_3PO_4$, 74% of kieselguhr and small quantities of propylene glycol, perfume and pigment.

EXAMPLE 2

An impression composition was prepared in the same manner as in Example 1 with the exception of using 6% sodium alginate (M/G ratio 1.3) having a viscosity of 100 cps, 6% of sodium alginate (M/G ratio 1.3) having a viscosity of 300 cps and 75% of kieselguhr.

EXAMPLE 3

An impression composition was prepared in the same manner as in Example 1 with the exception of using 10% sodium alginate (M/G ratio 1.3) having a viscosity of 100 cps, 5% of sodium alginate (M/G ratio 1.3) having a viscosity of 700 cps and 72% of kieselguhr.

EXAMPLE 4

An impression composition was prepared in the same manner as in Example 1 with the exception of using 10% sodium alginate (M/G ratio 1.3) having a viscosity of 100 cps and 3% of sodium alginate (M/G ratio 1.3) having a viscosity of 400 cps.

EXAMPLE 5

An impression composition was prepared in the same manner as in Example 1 with the exception of using 10% sodium alginate (M/G ratio 0.5) having a viscosity of 120 cps and 3% of sodium alginate (M/G ratio 1.3) having a viscosity of 690 cps.

EXAMPLE 6

An impression composition was prepared in the same manner as in Example 1 with the exception of using 10% sodium alginate (M/G ratio 0.75) having a viscosity of 120 cps and 3% of sodium alginate (M/G ratio 1.3) having a viscosity of 690 cps.

EXAMPLE 7

An impression composition was prepared in the same manner as in Example 1 with the exception of using 10% sodium alginate (M/G ratio 1.0) having a viscosity of 120 cps and 3% of sodium alginate (M/G ratio 1.3) having a viscosity of 690 cps.

COMPARATIVE EXAMPLE 1

An impression composition was prepared in the same manner as in Example 1 with the exception of using 12% of sodium alginate (M/G ratio 1.3) having a viscosity of 100 cps and 75% of kieselguhr.

COMPARATIVE EXAMPLE 2

An impression composition was prepared in the same manner as in Example 1 with the exception of using 12% of sodium alginate (M/G ratio 1.3) having a viscosity of 300 cps and 75% of kieselguhr.

Table 1 shows the M/G ratios of alginic acid and properties of the compositions of the above Examples and Comparative Examples. The ease of kneading was determined by kneading 6.7 g of the impression composition with addition of 15.7 cc of water for about 30 seconds to prepare a paste. The composition was evaluated as good in ease of kneading when it was compatible with water and kneadable easily free from dust. When the ease of kneading thus determined is ordinary, the result is evaluated as being usual. In case the ease of kneading is low, the result is shown as poor.

The strain on compression, permanent deformation and compressive strength were determined according to JIS T 6505 with use of the paste obtained in the above kneading test.

TABLE 1

|  | M/G ratio of alginic acid | | Properties | | | |
| --- | --- | --- | --- | --- | --- | --- |
|  | low-molecular-weight alginate | high-molecular-weight alginate | Ease of kneading | Strain in compression | Permanent deformation | Compressive strength |
| Ex. | | | | | | |
| 1 | 1.3 | 1.3 | good | 13.0% | 2.5% | 6000 g |
| 2 | 1.3 | 1.3 | good | 12.5% | 2.5% | 5500 g |
| 3 | 1.3 | 1.3 | good | 13.5% | 2.8% | 6500 g |
| 4 | 1.3 | 1.3 | good | 12.0% | 2.5% | 5000 g |
| 5 | 0.5 | 1.3 | good | 11.5% | 2.0% | 10000 g |
| 6 | 0.75 | 1.3 | good | 12.0% | 2.0% | 9000 g |
| 7 | 1.0 | 1.3 | good | 12.0% | 2.3% | 7500 g |
| Com. Ex. | | | | | | |
| 1 |  | 1.3 | good | 9.1% | 3.4% | 3500 g |
| 2 |  | 1.3 | usual | 9.5% | 3.5% | 4000 g |

We claim:
1. An impression composition, comprising:
   (a) an alginate;
   (b) calcium sulfate and/or lead silicate; and
   (c) a filler as its main components, the composition being characterized in that the alginate component comprises in combination an alginate having a distribution of molecular weights in a lower range and an alginate having a distribution of molecular weights in a higher range,
   wherein the alginate having a distribution of molecular weights in the lower range has a viscosity of about 50 to about 900 cps as measured at 25° C. using a B-type rotation viscometer when in the form of a 1% aqueous solution and the alginate having a distribution of molecular weights in the higher range has a viscosity of about 150 to about

1000 cps as measured under the same conditions, and the two alginates differ from each other by at least about 200 cps in viscosity.

2. an impression composition as defined in claim 1 wherein the proportion of the alginate having a distribution of molecular weights in the lower range and the alginate having a distribution of molecular weights in the higher range is in the range of 10:90 to 90:10 in weight ratio.

3. An impression composition as defined in claim 1 wherein the alginic acid molecules which constitute the alginate have an M/G ratio in the range of 0.3 to 1.

4. An impression composition as defined in claim 3 wherein the alginic acid molecules which constitute the alginate have an M/G ratio in the range of 0.5 to 1.

* * * * *